United States Patent [19]
Kim

[11] Patent Number: 5,976,573
[45] Date of Patent: *Nov. 2, 1999

[54] AQUEOUS-BASED PHARMACEUTICAL COMPOSITION

[75] Inventor: Soo-Il Kim, Maple Glen, Pa.

[73] Assignee: Rorer Pharmaceutical Products Inc., Greenville, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/678,465

[22] Filed: Jul. 3, 1996

[51] Int. Cl.$^6$ .............................. A61K 9/14; A61K 9/00; A61K 39/58

[52] U.S. Cl. .......................... 424/489; 424/497; 424/490; 424/45; 424/46; 424/492; 424/400; 514/951; 514/975; 514/174

[58] Field of Search ............................... 424/45, 46, 489, 424/490, 492, 497, 400; 514/951, 975, 174

[56] References Cited

U.S. PATENT DOCUMENTS

| | | | |
|---|---|---|---|
| 2,156,254 | 4/1939 | Manchey | 153/653 |
| 3,035,984 | 5/1962 | Mierswa | 424/78.13 |
| 3,780,176 | 12/1973 | Young | 154/39 |
| 3,809,294 | 5/1974 | Torgeson | 222/182 |
| 3,897,779 | 8/1975 | Hansen | 128/203.15 |
| 4,226,848 | 10/1980 | Nagai et al. | 514/772.1 |
| 4,250,163 | 2/1981 | Nagai et al. | 514/772.1 |
| 4,294,829 | 10/1981 | Suzuki et al. | 514/174 |
| 4,304,765 | 12/1981 | Shell et al. | 424/427 |
| 4,335,121 | 6/1982 | Phillipps et al. | 514/180 |
| 4,405,598 | 9/1983 | Brown | 424/45 |
| 4,407,792 | 10/1983 | Schoenwald et al. | 514/397 |
| 4,427,681 | 1/1984 | Munshi | 514/289 |
| 4,432,964 | 2/1984 | Shell et al. | 424/427 |
| 4,443,440 | 4/1984 | Anderson et al. | 514/177 |
| 4,478,818 | 10/1984 | Shell et al. | 424/426 |
| 4,782,047 | 11/1988 | Benjamin et al. | 514/174 |
| 4,933,168 | 6/1990 | Jones et al. | 424/45 |
| 4,983,595 | 1/1991 | Benjamin et al. | 514/174 |
| 5,000,936 | 3/1991 | Chibret | 424/43 |
| 5,300,302 | 4/1994 | Tachon et al. | 424/488 |
| 5,429,824 | 7/1995 | June | 424/489 |
| 5,432,147 | 7/1995 | Winston et al. | 504/101 |
| 5,432,148 | 7/1995 | Winston | 504/101 |
| 5,439,670 | 8/1995 | Purewal et al. | 424/45 |
| 5,443,833 | 8/1995 | Clark et al. | 424/400 |
| 5,461,081 | 10/1995 | Ali et al. | 514/772.3 |
| 5,492,937 | 2/1996 | Bogentoft et al. | 514/781 |
| 5,538,721 | 7/1996 | Babcock et al. | 424/78.04 |
| 5,540,930 | 7/1996 | Guy et al. | 424/427 |
| 5,543,434 | 8/1996 | Weg | 514/647 |

OTHER PUBLICATIONS

Settipane et al., Clinical Therapeutics, 1995, vol. 17, No. 2, pp. 252–263.
Kabayashi et al., 1995, Clincal Therapeutics, vol. 17, No. 3, pp. 503–513.
Physicans' Desk Reference, 1997, 51 Edition.
Copy of undated brochure entitled "Products and Services" of Valois Pharm.
"Nasalide", *Physician's Desk Reference*, pp. 2480–2481 (1995).
"Vancenase AQ", *Physician's Desk Reference*, pp. 2291–2292 (1995).
"Vancenase AQ 84 mcg", *Physician's Desk Reference*, pp. 2671–2672 (1998).
"Beconase AQ", *Physician's Desk Reference*, pp. 1076–1078 (1996).
"Flonase", *Physician's Desk Reference*, pp. 1098–1100 (1996).
"Nasarel", *Physician's Desk Reference*, pp. 2133–2134 (1996).
"Nasonex", *Physician's Desk Reference Supplement A*, pp. A99–A101 (1998).

*Primary Examiner*—Mary E. Mosher
*Assistant Examiner*—Ali R Salimi
*Attorney, Agent, or Firm*—Synnestvedt & Lechner LLP

[57] ABSTRACT

An aqueous pharmaceutical composition which is capable of being sprayed into the nasal cavity of an individual and which comprises: (A) a pharmaceutically effective amount of solid particles of medicament which is effective in treating a bodily condition by virtue of its being present on the mucosal surfaces of the nasal cavity; and (B) a suspending agent in an amount effective to maintain said particles dispersed uniformly in the composition and to impart to the composition the following thixotropic properties: (i) the viscosity of the position in unsheared form is relatively high, with the composition being in gel-like form; (ii) as the composition is subjected to shear (shaken) in preparation for spraying, the viscosity of the composition becomes relatively low and such that the composition in the form of a mist flows readily into the nasal passages for deposit on the mucosal surfaces of the nasal cavity; and (iii) in deposited form on the mucosal surfaces, the viscosity of the composition is relatively high and such that it resists being cleared from the mucosal surfaces by the inherent mucocillary forces which are present in the nasal cavity, a method of use of the composition and a method for preparation of the composition, including in preferred form the use of anti-inflammatory steroid, for example, triamcinolone acetonide, and an odorless form of the composition.

35 Claims, 2 Drawing Sheets

AQUEOUS-BASED PHARMACEUTICAL COMPOSITION

FIELD OF THE INVENTION

This invention relates to an aqueous-based pharmaceutical composition. More particularly, this invention relates to an aqueous composition containing a medicament that is effective in treating an abnormal bodily condition by virtue of its being present on the surfaces of the mucosa which line the nasal cavities.

The field of the present invention is described initially in connection with the treatment of particular forms of rhinitis, that is, an abnormal bodily condition that involves inflammation of the mucous membrane of the nose. It should be understood that the invention has broader applicability, as will be described below.

An estimated forty million Americans suffer from seasonal and perennial allergic rhinitis. Many more millions of individuals suffer from this condition worldwide. Symptoms of seasonal and perennial allergic rhinitis include nasal itch, congestion, runny nose, sneezing and watery eyes. Seasonal allergic rhinitis is commonly known as "hay fever". It is caused by allergens which are present in the air at specific times of the year. Tree pollens in the springtime of the year are examples of such allergens. Perennial allergic rhinitis is caused by allergens which are present in the environment year-round. Examples of such allergens are dust mites, mold, mildew, and pet dander.

It is known to treat such forms of rhinitis with medicaments such as, for example, steroidal anti-inflammatory agents. Triamcinolone acetonide is an example of a widely used steroidal anti-inflammatory agent. Such an agent is generally used by spraying it into the nasal passages of the human patient where it deposits on surfaces of the mucosa which line the nasal cavities. In this position, the medicament exerts its pharmacological action as it is in contact with bodily tissues and interacts with steroid receptors.

For maximum effectiveness, a pharmaceutical composition containing the aforementioned type of medicament must have a combination of desired properties. For example, the nature of the pharmaceutical composition containing the medicament should be such that the medicament is delivered readily to all portions of the nasal cavities (the target tissues) where it performs its pharmacological function. In addition, the medicament should remain in contact with the target tissues for relatively long periods of time. The longer the medicament remains in contact with the target tissues, the greater the opportunity for the medicament to perform its function. In order to remain in contact with the target tissues, the medicament must be capable of resisting those forces in the nasal passages that function to remove particles from the nose. Such forces, referred to as "mucocillary clearance", are recognized as being extremely effective in removing particles from the nose in a rapid manner, for example, within 10–30 minutes from the time the particles enter the nose.

Other desired characteristics of the pharmaceutical composition are that it not contain ingredients which cause the user discomfort, that it have satisfactory stability and shelf-life properties, and that it not include constituents that are considered to be detrimental to the environment, for example, ozone depletors.

The present invention relates to a pharmaceutical composition which has a combination of properties that make it particularly effective and suitable for relieving abnormal bodily conditions that can be treated by depositing the composition on the surface of the mucosa which line the nasal passages.

Reported Developments

The following patents disclose pharmaceutical compositions which contain various types of medicaments, including medicaments which function to treat an abnormal bodily condition by virtue of the medicament's being present on the mucosal surfaces of the nasal cavities, U.S. Pat. Nos. 3,780,176; 3,809,294; 3,897,779; 4,405,598; 4,250,163; 4,294,829; 4,304,765; 4,407,792; 4,432,964; 4,443,440; 4,478,818; and 5,439,670.

In contrast to compositions described in the aforementioned patents, the pharmaceutical composition of the present invention is aqueous based.

SUMMARY OF THE INVENTION

In accordance with the present invention, there is provided an aqueous pharmaceutical composition which is capable of being sprayed into the nasal cavity of an individual and which comprises: (A) a pharmaceutically effective amount of solid particles of medicament which is effective in treating a bodily condition by virtue of its being present on the mucosal surfaces of the nasal cavity; and (B) a suspending agent in an amount effective to maintain said particles dispersed uniformly in the composition and to impart to the composition the following thixotropic properties: (i) the viscosity of the position in unsheared form is relatively high, with the composition being in gel-like form; (ii) as the composition is subjected to shear (shaken) in preparation for spraying, the viscosity of the composition becomes relatively low and such that the composition in the form of a mist flows readily into the nasal passages for deposit on the mucosal surfaces of the nasal cavity; and (iii) in deposited form on the mucosal surfaces, the viscosity of the composition is relatively high and such that it resists being cleared from the mucosal surfaces by the inherent mucocillary forces which are present in the nasal cavity.

In preferred form, the medicament comprises an anti-inflammatory steroid, most preferably triamcinolone acetonide. Also in preferred form, the composition of the present invention is odorless and includes a quaternary ammonium compound, preferably benzalkonium chloride, and a chelating agent, preferably disodium ethylenediamine tetraacetate (EDTA).

Another aspect of the present invention comprises a method for applying solid particles of a medicament to the mucosal surfaces of the nasal cavities comprising spraying a dose of an aqueous pharmaceutical composition containing said medicament into each of the nasal cavities, said dose containing a pharmaceutically effective amount of said medicament, said composition including also a suspending agent in an amount which is effective in maintaining said particles dispersed uniformly in the composition and in imparting to the composition thixotropic properties such that pharmaceutically effective amounts of the medicament are deposited at least on each of the mucosal surfaces of the anterior regions of the nose, the frontal sinus and the maxillary sinuses and on each of the mucosal surfaces which overlie the turbinates covering the conchas and such that portions of said amounts are retained on each of said mucosal surfaces for at least about an hour.

In preferred form, the composition is applied to the nasal cavities by spraying utilizing a precompression pump.

Still another aspect of the present invention comprises a method for preparing an aqueous pharmaceutical composition comprising a medicament in the form of solid particles, a dispersing agent for wetting said particles, and a suspending agent for maintaining said particles substantially uniformly dispersed in the composition and for imparting to the composition thixotropic properties comprising: (A) forming an aqueous solution of the dispersing agent and combining the solution with the solid particles to form a suspension of the particles; (B) adding the suspending agent to an aqueous acidic solution to form a thixotropic suspension; and (C) combining each of the suspensions by introducing one of the suspensions into the bottom of the other suspension.

In preferred form, the suspension of solid particles of medicament is introduced into the bottom of the thixotropic suspension.

The present invention affords numerous and important advantages in the treatment of a condition that involves application of a medicament to the surface of the mucosa which line the nasal cavities. As will be understood from a reading of the example section of the application, the present invention provides means for delivering a medicament readily to the many portions of the nasal cavities where it can perform its pharmacological function. In accordance with the present invention, the medicament remains in contact with the target tissues for relatively long periods of time, for example, at least about an hour and for even two or more hours. Furthermore, the composition of the present invention is capable of being formulated in a manner such that ingredients which cause the user discomfort are absent, the composition has satisfactory stability and shelf-life properties, for example, one to two years, and it does not include constituents that are considered to be detrimental to the environment.

DETAILED DESCRIPTION OF THE INVENTION

Figure 1:
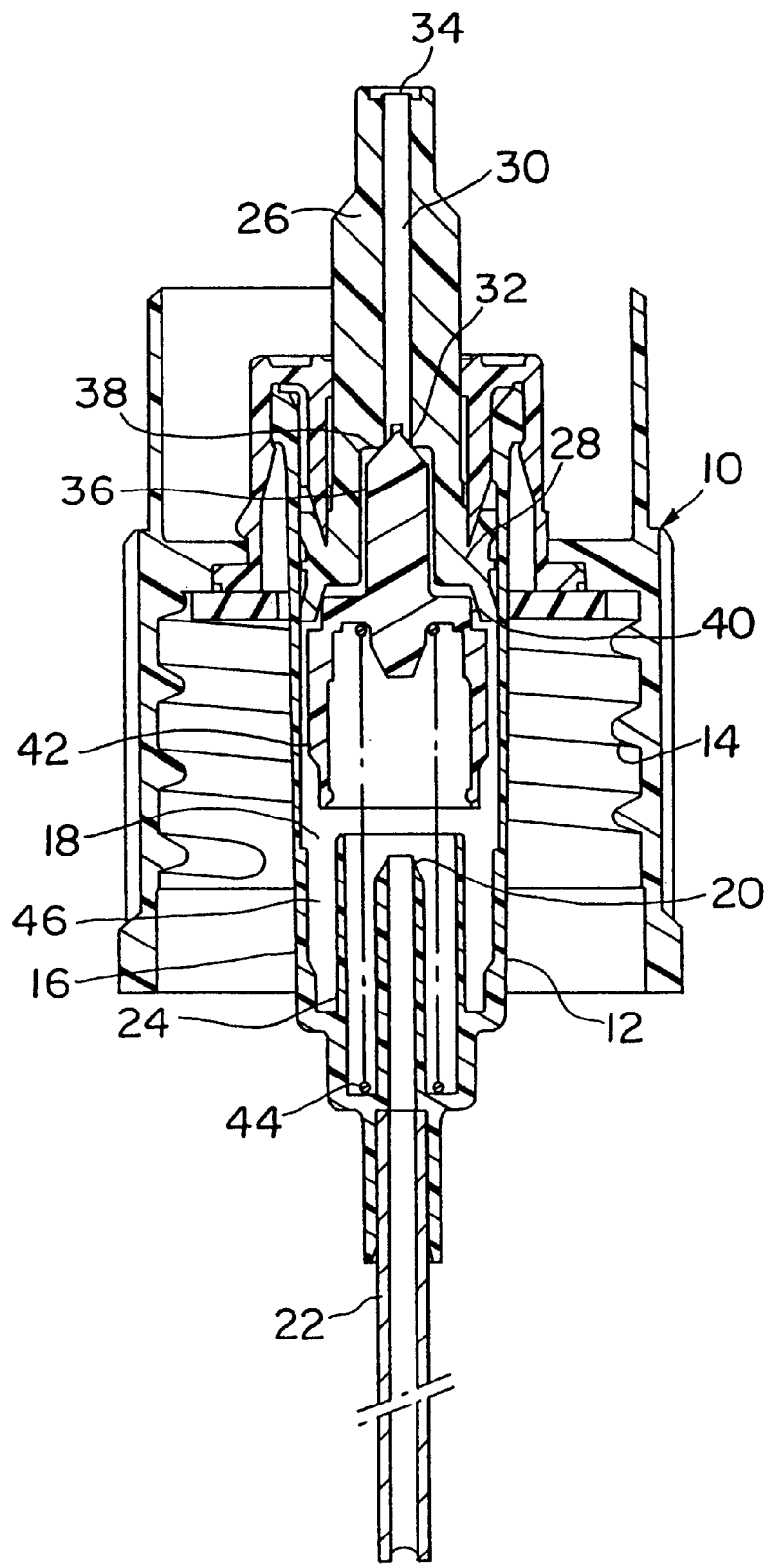
FIG. 1 is a cross-sectional view of a precompression pump which is shown in its rest position and which can be used in applying the composition of the present invention to the nasal cavities.

The water-based composition of the present invention comprises a medicament in the form of solid particles and other pharmaceutically acceptable ingredients, that is, materials which are compatible with the medicament, which are not toxic to the body under the conditions of use and which avoid or minimize tissue irritation. As will be appreciated from the description which follows, there is no need to use in the water-based composition of the present composition a propellant which is a necessary ingredient of aerosol products.

Water is present in the composition in a major amount. Typically, it will comprise at least about 85 wt. % of the composition and more typically at least about 90 wt. % of the composition.

The medicament for use in the practice of the present invention is one which is capable of treating an abnormal bodily condition by virtue of its being present on the mucosal surfaces of the nasal cavities. Examples of such a medicament are steroidal and non-steroidal anti-inflammatory agents, beta agonists and bronchodilators. Such a medicament provides the relief of nasal symptoms caused by upper respiratory tract inflammation and allergic rhinitis.

It is believed that the medicament that will be used most widely in the practice of the present invention will be an anti-inflammatory steroid such as, for example, clomethasone, dexamethasone, fluticasone, prednisolone and triamcinolone acetonide. Such steroidal compounds are relatively potent drugs which, when applied locally, are highly effective with reduced systemic exposure. Triamcinolone acetonide is a preferred medicament for use in the practice of the present invention.

A medicament such as triamcinolone acetonide is substantially water insoluble and hydrophobic. For use in the present invention, such medicament is present in the composition in the form of solid particles that are dispersed in the aqueous phase of the composition. The sizes of the particles are such that the medicament is capable of being uniformly dispersed in the composition. For this purpose, the size of the particles should be no greater than about 50 microns. Preferably the particles have an average size of about 1 to about 20 microns.

The medicament is present in the composition in a pharmaceutically effective concentration. Such concentration will vary depending on the particular medicament or mixture of medicaments used, the condition to be treated and the nature of the individual being treated. For guideline purposes, it is recommended that the medicament comprise about 0.001 to about 2 wt. % of the composition, preferably about 0.01 to about 0.2 wt. % of the composition.

The composition of the present invention contains also a pharmaceutically acceptable excipient which is effective in forming a thixotropic suspension of the solid particles of medicament comprising the composition. The excipient is present in an amount which maintains the particles of medicament suspended in the composition during non-use and during spray of the composition into the nasal cavity, and also when the composition is deposited on the mucosal surfaces of the nasal cavities. The thixotropic nature of the composition at rest (not subject to shear) can be described as a gel in which the particles of medicament are dispersed and suspended substantially uniformly. The viscosity of the composition at rest is relatively high, for example, about 400 to about 1000 cp. As the composition is subjected to shear forces, for example, upon being subjected to forces involved in its being agitated before spraying, the viscosity of the composition decreases (for example, to about 50 to about 200 cp) and it flows readily through the spray device and exits therefrom in the form of a fine plume which infiltrates and deposits on the mucosal surfaces of at least the following parts of the nose: the anterior regions of the nose (frontal nasal cavities); the frontal sinus; the maxillary sinuses; and the turbinates which overlie the conchas of the nasal cavities. Thus, the thixotropic composition is such that it comprises a freely flowable liquid, and in sprayed form, a fine mist that finds its way to and deposits on the desired mucosa. In deposited and relatively unstressed form, the composition increases in viscosity and assumes its gel-like form which includes particles of the medicament suspended therein and which resists being cleared from the nasal passages by the inherent mucocillary forces that are present in the nasal cavities. Tests have shown that amounts of the deposited composition remain on the mucosal surfaces for relatively long periods of time, for example, at least one hour and even up to two or more hours.

For convenience, the viscosity of the composition at rest is referred to as the "setting viscosity" and the viscosity of a composition which is shaken is referred to as the "shear viscosity". As mentioned above, the setting viscosity of the composition should be sufficiently high to hold and maintain the particles of medicament dispersed substantially uniformly in the composition and to retain for an extended period of time the composition on the mucosal surfaces on which it is deposited in the nasal cavities, that is, the composition resists being swept away by the mucocillary forces which are present in the nasal cavities. The shear viscosity of the composition is sufficiently low to permit the composition to flow freely through the pump orifice and to break up into a fine mist.

Suitable values for the setting viscosity and for the shear viscosity of the composition can be determined for a particular composition, taking into account also the particular means used to apply the composition to the nasal cavities. By way of example, a setting viscosity of about 400 to about 800 cp is recommended for a composition containing an anti-inflammatory steroid, for example, triamcinolone acetonide. A recommended shear viscosity for such a composition is about 50 to about 200 cp. Viscosity is measured using a Brookfield Synchro-Letric viscometer (Model LVT). The viscosity is measured at 20° C. The setting viscosity is measured after mixing at 30 rpm for 30 seconds. The shear viscosity is measured by mixing at 30 rpm for 30 seconds after mixing on a Burrell wrist-action shaker at full speed for 5 minutes.

Any pharmaceutically acceptable material which is capable of maintaining the solid particles of medicament dispersed substantially uniformly in the composition and of imparting to the composition the desired thixotropic properties can be used. Such material is referred to as a "suspending agent". Examples of suspending agents include carboxymethylcellulose, veegum, tragacanth, bentonite, methylcellulose, and polyethylene glycols. A preferred suspending agent is a mixture of microcrystalline cellulose and carboxymethylcellulose, the former being present preferably in a major amount, most preferably in an amount of about 85 to about 95 wt. %, with the latter constituent comprising about 5 to about 15 wt. % of the mixture.

The amount of suspending agent comprising the composition will vary depending on the particular medicament and amount used, the particular suspending agent used, the nature and amounts of the other ingredients comprising the composition, and the particular viscosity values that are desired. Generally speaking, it is believed that the most widely used compositions will comprise about 1 to about 5 wt. % of the suspending agent.

The pharmaceutical composition of the present invention includes preferably other ingredients which impart desired properties to the composition.

A composition which contains a medicament which is hydrophobic includes preferably a pharmaceutically acceptable dispersing agent which functions to wet the particles of medicament to facilitate dispersion thereof in the aqueous phase of the composition. The amount of dispersing agent should be sufficient to wet the hydrophobic particles of medicament within a short time, for example, about 5 to about 60 minutes, as the aqueous dispersion of particles is mixed with conventional mixing equipment. It is preferred to use an amount of dispersing agent which will not cause foaming of the dispersion during mixing thereof. It is recommended that the dispersing agent comprise about 0.001 to about 0.01 wt. % of the composition.

Any dispersing agent which is effective in wetting the particles and which is pharmaceutically acceptable can be used. Examples of dispersing agents that can be used are fatty alcohols, esters, and ethers, including, for example, those sold under the trademarks Pluronic, Tergitol, Span, and Tween. It is preferred to use a hydrophilic, non-ionic surfactant. Excellent results have been achieved utilizing sorbitan polyoxyethylene sorbitan monooleate which is available under the trademark Polysorbate 80.

It is known that various medicaments of the type that can be used in the composition of the present invention tend to degrade in the presence of water as a result of being oxidized. This can be prevented or deterred by use of an anti-oxidant. Examples of pharmaceutically acceptable antioxidants that can be used in the composition include ascorbic acid, sodium ascorbate, sodium bisulfite, sodium thiosulfate, 8-hydroxy quinoline, and N-acetyl cysterine. It is recommended that the composition comprise about 0.001 to about 0.01 wt. % of the anti-oxidant.

Also, for stability purposes, the composition should be protected from microbial contamination and growth. Examples of pharmaceutically acceptable anti-microbial agents that can be used in the composition include quaternary ammonium compounds, for example, benzalkonium chloride, benzethonium chloride, cetrimide, and cetylpyridinium chloride; mercurial agents, for example, phenylmercuric nitrate, phenylmercuric acetate, and thimerosal; alcoholic agents, for example, chlorobutanol, phenylethyl alcohol, and benzyl alcohol; antibacterial esters, for example, esters of para-hydroxybenzoic acid; and other anti-microbial agents such as chlorhexidine, chlorocresol, and polymyxin. It is recommended that the composition comprise about 0.001 to about 1 wt. % of the anti-microbial agent.

As mentioned above, an aspect of the present invention comprises a composition which is odorless and which contains a mixture of stabilizing agents which function as an anti-oxidant and as an anti-microbial agent. The mixture comprises a quaternary ammonium compound that has antimicrobial properties and a material which is generally recognized as a chelating agent. The use in the composition of this combination of materials with the medicament, for example, triamcinolone acetonide, results in a highly stable composition that is resistant to oxidative degradation and to the growth of bacteria and the like. In preferred form, the mixture comprises benzalkonium chloride and disodium ethylenediamine tetraacetate.

The odorless composition generally will comprise about 0.004 to about 0.02 wt. % of the quaternary ammonium compound and about 0.01 to about 0.5 wt. % of the chelating agent. By virtue of the use of the aforementioned mixture of compounds, it is not necessary to include in the composition a material which is considered an anti-oxidant.

The composition of the present invention includes preferably an iso-osmotic agent which functions to prevent irritation of nasal mucosa by the composition. Dextose in anhydrous form is a preferred iso-osmotic agent. Examples of other pharmaceutically acceptable iso-osmotic agents which can be used include sodium chloride, dextrose and calcium chloride. It is recommended that the composition comprise up to about 5 wt. % of the iso-osmotic agent.

The pH of the composition will vary depending on the particular medicament used and taking into account biological acceptance and the stability of the medicament. Typically, the pH of the composition will fall within the range of about 4.5 to about 7.5. The preferred pH for a composition which contains triamcinolone acetonide is about 4.5 to about 6, most preferably about 5. Examples of pharmaceutically acceptable materials which can be used to adjust the pH of the composition include hydrochloric acid and sodium hydroxide.

The composition of the present invention can be prepared in any suitable way. In preferred form, an aqueous suspension of the solid particles of medicament and dispersing agent is formed and combined with an aqueous suspension which contains the suspending agent. The former is preferably prepared by adding the medicament to an aqueous solution of the dispersing agent and mixing thoroughly. The latter is prepared by acidifying the water (pH about 4.7 to about 5.3) prior to adding the suspending agent. In particularly preferred form, an aqueous solution of the quaternary compound (anti-microbial agent) is added to the aqueous suspension of medicament, and the other ingredients (for example, iso-osmotic agent, anti-oxidant or chelating agent) are added to the thixotropic suspension. Each of the aforementioned batches of composition is mixed thoroughly before being combined. The preferred means of combining the batches of composition is to introduce one of the batches, preferably the "medicament" batch into the bottom of the other batch, for example, by pumping the batch upwardly through the other batch. The composition comprising the combined batches is mixed thoroughly. Use of the preferred method of preparation provides an efficient and effective way for formulating a composition that has the solid particles of medicament substantially uniformly dispersed therein while avoiding problems that are generally associated with the preparation of water-based pharmaceutical compositions, for example, excessive foaming and non-uniformity of the particle dispersement.

The amount of medicament applied to each of the nasal passages will vary depending on the particular medicament used, the nature of the condition being treated and the nature of the individual being treated. For guideline purposes, it is suggested that the unit dosage applied to one of the nasal cavities comprise about 200 to about 450 mcg of the medicament. Use of the preferred form of the composition of the present invention provides the advantage that the composition can be applied effectively once daily. For such once-a-day dose, it is recommended that the amount of medicament, for example, triamcinolone acetonide, applied to one of the nostrils comprise about 100 to about 130 mcg.

The preferred means for applying the pharmaceutical composition of the present invention to the nasal passages is by use of a precompression pump. A preferred precompression pump is model VP7 manufactured by Valois SA of France and marketed in the United States by Valois of America, 15 Valley Drive, Greenwich, Conn. 06831.

Referring to FIG. 1, the precompression pump 10 has a housing 12 and includes means such as screw threads 14 for connecting the pump 10 to a container of the composition. The housing 12 includes a cylindrical outer wall 16 defining a hollow tube 18, a housing inlet 20 connected to a dip tube 22 through which the liquid enters the pump 10 from the container (not shown), and a cylindrical internal wall 24 positioned between the inlet 20 of the inlet tube 22 and the outer wall 16.

A stem 26 extends from the top of the housing 12 and has a bottom section 28 positioned within the housing hollow tube 18 slidably engaging the outer wall 16 to form a liquid seal. A center tube 30 within the stem connects a stem inlet 32 to a stem outlet 34 through which the liquid is dispensed to an atomizer to generate a spray.

A clapper 36 is slidably positioned within the hollow tube 18 between the stem 26 and the internal wall 24. The clapper 36 has a head section 38 which engages the stem inlet 32 to prevent liquid flow therethrough, a shoulder 40, and a bell-shaped bottom section 42 designed to slide over and seal against the housing internal wall 24 when the clapper 36 is moved downwardly. A spring 44 between the bottom of the housing 12 and the underside of the clapper head section 38 biases the clapper head to engage and seal the stem inlet 32.

The pump 10 operates as follows. In the rest position, as shown in FIG. 1, the clapper head 38 seals the stem inlet 32 to prevent liquid flow. The dosage chamber 46 is filled with the composition. It is seen that the volume of the dosage chamber 46 is defined by the housing outer wall 16, the housing inner wall 24, the clapper 36, and the stem 26. The dosage volume is controlled by the dimensions of these various elements which define the dosage chamber 46.

Figure 2:
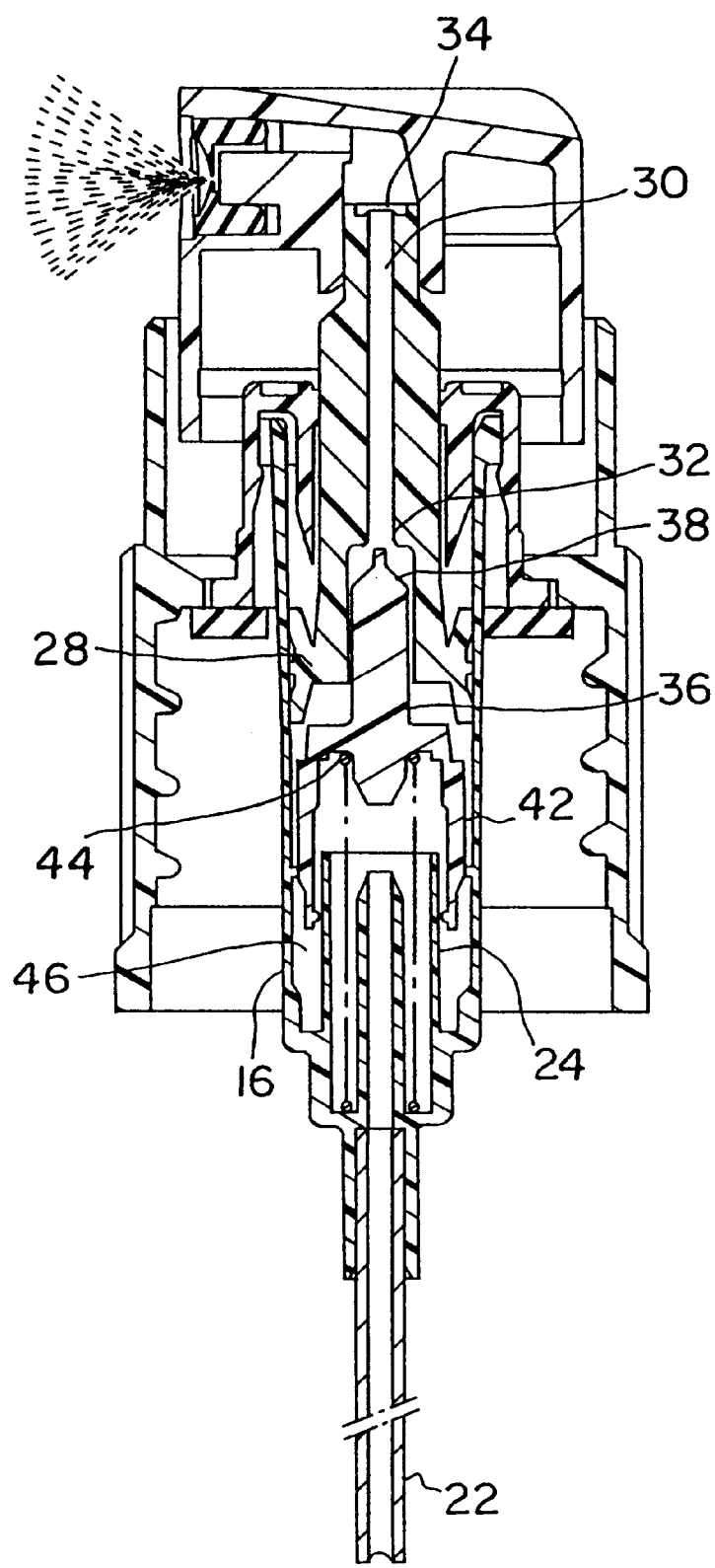
FIG. 2 is a cross-sectional view of the pump of FIG. 1 shown in its actuated position.

The action of the user's finger depressing the stem 26 causes the stem 26 and clapper 36 to move downwardly. As seen in FIG. 2, the dose chamber 46 is closed by the bottom section 42 of the clapper engaging the housing internal wall 24. (FIG. 2 shows a side spray nozzle, it being understood that this is for illustrative purposes only and that other forms may be used such as a top spray nozzle.) Further pressure causes an increase in hydraulic pressure in the composition now isolated in the dosage chamber 46 relative to the pressure of the composition within the housing internal wall 24. As liquid is essentially incompressible, the increased hydraulic pressure of the composition in the dosage chamber 46 creates a net downward force on the clapper 36. Once this downward force exceeds the upward force on the clapper 36, such as from the spring 44, the clapper moves further downwardly away from the stem 26 to open the stem inlet 32 and allow the liquid composition to flow from the dosage chamber 46 to the stem outlet 34 to generate the spray.

After the spray, when action of the user's finger releases the stem, the spring 44 returns the clapper 36 to engage and seal the inlet 32 and return it to its rest position. This movement creates a vacuum which draws the composition into the dosage chamber 46 through the housing inlet 20 of the inlet tube 22 for the next dosage.

A precompression pump provides a spray superior to that of conventional pumps. During normal usage, the precompression pump will deliver a full dosage of the composition. As previously described, no composition will be sprayed until the hydraulic pressure of the composition reaches a "threshold" pressure within the pump sufficient to disengage the clapper 36 from the stem inlet 32. Once the clapper 36 disengages the stem inlet 32, the hydraulic pressure provided by the user's finger forces the predetermined amount of composition into the stem inlet 32 for spraying. Thus, no spray is released prior to reaching the threshold pressure, and the entire dosage is released after the threshold pressure is reached. With conventional pumps, an amount less than the full dosage can be released if a sufficient amount of force is not applied or if it is not applied in a proper manner. With the precompression pump, it is extremely difficult to release less than the full dosage when normally using the pump.

Another advantage of the precompression pump is that atomization of the spray is ensured. With conventional pumps, sufficient pressure may not be provided by the user to properly atomize the spray. The precompression pump, however, does not release composition until the threshold pressure is reached, which is designed to be sufficient for atomization.

Furthermore, the precompression pump is less user dependent. Since it will not spray until the threshold pressure is reached, the force and method of depression applied by the user has less of an effect on the spray.

EXAMPLES

The following examples are illustrative of the present invention.

Example 1

A preferred pharmaceutical composition of the present invention is described below.

| COMPONENT | Wt. % | Amount, mg |
|---|---|---|
| triamcinolone acetonide, USP. micronized topical grade (TAA) | 0.055 | 9.075 |
| mixture of microcrystalline cellulose and carboxymethyl-cellulose sodium, NF (Avicel CL-611) | 2.0 | 330.00 |
| Polysorbate 80, NF surfactant | 0.004 | 0.66 |
| disodium ethylenediamine tetraacetate, USP | 0.05 | 8.25 |
| benzalkonium chloride (BZCl) solution, 50 wt. % of BzCl, NF | 0.03 | 4.95 |
| dextrose (anhydrous), USP | 5.0 | 825.00 |
| purified water, USP | 92.86 | 15,322 |
| diluted hydrochloric acid, NF | * | * |
| 0.1 N NaOH solution | * | * |
| TOTAL WEIGHT | | 16.5 g |

*Used for pH adjustment.

The composition is prepared by utilizing a two-container method to mix the individual ingredients listed above. A large batch of the composition is prepared in the manner described below. A 16.5 g portion is extracted from the large batch to fill a spray bottle as described below also.

To a stainless steel kettle equipped with a variable speed sweep mixer, a variable speed agitator, and a fixed speed dispersator, about 500 kg of purified water are added. About 0.4125 kg of disodium ethylenediamine tetraacetate (hereafter "EDTA") and 41.25 kg of dextrose are added to the water. After the above ingredients are mixed for about 25 minutes, the dispersator and agitator are stopped and the sweep mixer is turned on. About 0.6 kg of diluted hydrochloric acid ("HCl") solution is added to the EDTA and dextrose solution. The dispersator is restarted, followed by the addition of about 16.5 kg of a mixture of microcrystalline cellulose and carboxymethylcellulose sodium to the acidified EDTA/dextrose solution. The resulting suspension is homogenized by continued mixing for about 10 minutes. All mixers are then stopped for the kettle to be scraped. Homogenization is resumed by using the sweep mixer and dispersator for about 15 minutes.

To a second stainless steel kettle equipped with a fixed speed dispersator and fixed speed mixer, about 250 kg of purified water are added. The dispersator and mixer are turned on, followed by the addition of about 0.033 kg of Polysorbate 80 (wetting agent). After about 10 minutes of mixing, about 1 liter of the solution is withdrawn. With continued mixing, about 0.45375 kg of triamcinolone acetonide TAA is added to the kettle containing the dissolved surfactant. The "TAA" container is rinsed with the withdrawn surfactant solution and the rinse is added to the kettle. The TAA suspension is homogenized for about 25 minutes using the dispersator and mixer. With the dispersator turned off, about 0.2475 kg of the benzalkonium chloride (BzCl) solution are added and dissolved into the resulting TAA dispersion. The "BzCl" container is rinsed with approximately 1 kg of purified water and the rinse is added to the TAA dispersion. The "TAA" dispersion is transferred to the "thixotropic" portion of the composition by pumping the TAA dispersion through the bottom outlets of the two kettles. The "TAA" kettle is rinsed with about 10 kg of purified water and the rinse is added to the composition comprising the combined TAA dispersion and thixotropic portion.

The pH of the resulting composition is then determined. The target pH of preferred embodiments of the present invention ranges from about 4.7–5.3. If needed, the pH is adjusted by adding, most preferably, either: 1) diluted HCl, NF which is diluted further with purified water (20 parts water:1 part diluted HCl, NF); or 2) 0.1N NaOH solution (prepared by dissolving 4 g of sodium hydroxide, NF in purified water, and diluting to 1000 ml). The amount of added HCl or NaOH solution is measured, and an amount equal to this is withdrawn from 4.5 kg of purified water. After the withdrawn portion is removed, the remaining water is added to the composition, followed by homogenization using the dispersator for about 2 minutes.

The composition is then transferred to a kettle equipped with a fixed-speed mixer. The mixer is set at about 6 rpm and the composition is mixed thoroughly. The composition has a pH of about 4.8 and at rest (unstressed—not subjected to shear) comprises a gel-like suspension. The TAA particles are uniformly dispersed throughout the composition.

A 16.5 gram portion of the composition is then added to a HDPE round 20 ml bottle. Before the bottle is filled, about 0.2u filtered compressed air is blown inside the bottle. The bottle is capped with a metering pump. The metering pump is a Valois VP7/100S pump having a dip tube, an actuator, an overcap, and a safety clip.

Example 2

Another composition within the scope of the present invention is prepared utilizing the method and ingredients described in Example 1, but with the following changes. In the first mentioned kettle, the EDTA, dextrose, and water are mixed for about 10 minutes measured from the time that the EDTA and dextrose are added to the water. About 0.53 kg diluted HCl, NF is added to the EDTA and dextrose solution contained in the kettle.

Preparation of the "TAA" portion of the composition and transfer thereof to the "thixotropic" portion of the composition is effected as described in Example 1. During the step of pH adjustment, which takes place after the transfer of the "TAA" portion to the "thixotropic" portion, the amount of added HCl or NaOH solution is measured, and an equal amount is withdrawn from 4.57 kg of purified water. After the withdrawn portion is removed, the remaining water is added to the composition, followed by homogenization using the dispersator for about 2 minutes. The pH of the composition is about 5. The particles of TAA are dispersed uniformly throughout the composition. The bottle-filling process is the same as described in Example 1.

The following constitutes a description of examples of how the composition of the present invention can be used.

Compositions such as those described in Examples 1 and 2 can be inhaled nasally for effective treatment of allergic rhinitis symptoms. As described in Examples 1 and 2, each of the compositions is packaged in a metered pump spray bottle which holds about 16.5 g of the composition.

A dose of the composition can be delivered to a human patient by spraying the composition into each of the patient's nasal cavities. For dose delivery, the precompression metering pump (Valois VP7/100S) is placed in a patient's nostril and is then actuated by the patient, resulting in a spray into the nasal cavity. After initial priming, each actuation of the pump delivers from the nasal actuator about 100 mg of composition containing about 55 mcg of TAA. Each bottle of composition will provide at least about 120 metered doses. For the exemplified compositions, the recommended once-daily dosing for adults and children 12 years and older begins at about 220 msg of TAA, equivalent to two sprays in each nostril.

A composition comprising the formulation of Examples 1 and 2 was administered to two volunteer patients. Post administration, the patients were evaluated by positron emission tomography in order to determine 1) the amount of time it took for the maximum dose of the TAA medicament to be delivered to various regions of interest within the nasal cavity, and 2) the amount of TAA medicament deposited on the regions of interest over a two hour time period. For purposes of the evaluation, the volume of the head region was segmented into 104 distinct regions of interest. Included in the regions of interest are the following target sites: the frontal cavities, frontal sinus, maxillary sinuses, superior concha, and inferior concha. The results of evaluation indicate a rapid distribution of the TAA medicament to the target regions of the nose.

For one of the volunteers, the maximum amount of the TAA medicament which came in contact with the concha regions was about 65% of the total dose delivered to the nose and this occurred at about 45 seconds post dose. About 46% of the total dose came in contact with the inferior concha and about 19% of the total dose came in contact with the superior concha. The amount of TAA medicament in contact with the concha tissues declined with time, until a constant value of about 3.4–4% of the total dose administered remained in the concha tissues at the final time period. The maximum amount of the TAA medicament which came in contact with the frontal cavity region was about 41% and this occurred at about 45 seconds post dose. The maximum amount of the TAA medicament contacting the frontal cavity region slowly declined as a function of time, maintaining constant levels of about 12% at two hours post-dose. Based upon this information, the frontal cavity is considered a target tissue since the deposited composition is maintained as a reserve or back-up supply of the medicament. The slow migration of the viscous composition back over the concha tissues via mucocillary clearance suggests that TAA medicament is continuously bathing the target tissues, thus accounting for the efficacy of the preferred once-daily dosing. Interestingly, the drug appears to enter into both the maxillary and frontal sinuses. The data suggest that the particles of the medicament are carried into the sinuses due to the turbulent airflow during nasal inhalation. The maximum amount deposited was approximately 3.5% and 3.9% of the dose into the frontal and maxillary sinuses respectively, and this occurred within about 30 seconds after post dose. The data indicate that the TAA medicament is cleared from the frontal sinus within 1 hour and that approximately 1% of the medicament is still present at the two hour acquisition sampling time in the maxillary sinuses.

For the other volunteer, the maximum amount of the drug which came in contact with the concha regions was about 53% of the total dose delivered to the nose, about 25% associated with the superior concha and about 75% associated with the inferior concha. The maximum amount of the TAA medicament which came in contact with the superior concha region occurred at about 25 seconds post dose and for the inferior concha region at about 3.5 minutes. This data suggests that the TAA medicament is moving into the concha region from the frontal cavity area. At about two hours post-administration, about 6–8% of the administered dose still remained in contact with the concha regions, with the medicament slowly being cleared from this target site.

The maximum amount of the TAA medicament which came in contact with the frontal cavity was about 55% of the total dose delivered to the nose and this occurred within about 30 seconds post dose. The medicament appeared to leave the nasal cavity slowly with approximately 22% of the dose still resident after two hours. A small percentage of the administered dose of the TAA medicament came into contact with the maxillary and frontal sinuses. The maximum amount was deposited within about 30 seconds post dose, with values around 3.5% for the frontal sinus and about 2% for the maxillary sinus. These values remained relatively constant, with approximately 0.5% to 1% of the dose still remaining in the sinuses after two hours.

The evaluation included also a determination of the percentage of the TAA medicament remaining on the target sites two hours after it was administered to each of the patients. This percentage was determined by dividing the amount remaining in each region of interest by the total amount remaining in the 104 regions of interest. The results from this evaluation indicate that greater than 85% of the dose was directly deposited on the target sites, including the frontal cavity, frontal sinus, maxillary sinuses, superior concha, and inferior concha.

For the first of the volunteers discussed above, the results indicate that about 47.9% of the total TAA medicament remained deposited in the frontal cavity two hours after the drug was administered. The percentage of the total medicament deposited in the inferior concha region two hours post administration (about 27.8%), when combined with the superior concha region deposited amount (about 8.6%), accounted for about 36.4% of the amount remaining of the dose administered to the principal target region of the nose. Over a two-hour period of time, about 1.2% of the dose was deposited on the frontal sinus while about 3% of the dose was deposited in the maxillary sinus region. Summing the percentages of the administered drug remaining on the target sites two hours after the medicament was administered indicates that about 88.5% of the dose administered was deposited directly onto target tissues over the two-hour serial sampling period.

For the second of the volunteers discussed above, the results indicate that about 52.2% of the dose administered remained deposited in the frontal cavity two hours post-drug administration. About 23.5% of the dose remained deposited on the inferior concha and about 6.9% of the dose remained deposited on the superior concha. Total percentage of the dose remaining deposited on the concha region was about 30.4% of the overall dose delivered. Values for the frontal and maxillary sinuses were about 1.6% and about 1.4% of the dose administered, respectively. Summing the percentages of the administered drug remaining on the target sites two hours after the drug was administered indicates that about 85.6% of the dose administered was deposited directly onto target tissues over the two hour serial sampling period.

It should be appreciated that the present invention provides effective and improved means for relieving patients from unsettling abnormal bodily conditions.

I claim:

1. An aqueous pharmaceutical composition which is capable of being sprayed into the nasal cavity of an individual and which comprises: (A) a pharmaceutically effective amount of solid particles of triamcinolone acetonide which is effective in treating an abnormal bodily condition by virtue of its being present on the mucosal surfaces of the nasal cavity; and (B) a suspending agent in an amount effective to maintain said particles dispersed uniformly in the composition and to impart to the composition the following thixotropic properties: (i) the viscosity of the composition in unsheared form is relatively high, with the composition being a gel having said particles suspended therein; (ii) as the composition is subjected to shear (shaken) in preparation for spraying, the viscosity of the composition becomes relatively low and such that the composition in the form of a mist flows readily into the nasal passages for deposit on the mucosal surfaces of the nasal cavity; and (iii) in deposited form on the mucosal surfaces, the viscosity of the composition is relatively high and such that it resists being cleared from the mucosal surfaces by the inherent mucocillary forces which are present in the nasal cavity.

2. The composition of claim 1 wherein said composition includes microcrystalline cellulose and carboxymethyl cellulose sodium and a chelating agent.

3. The composition of claim 2 wherein said chelating agent is disodium ethylene diamine tetraacetate.

4. The composition of claim 2 wherein said composition includes dextrose.

5. An aqueous pharmaceutical composition which is capable of being sprayed into the nasal cavity of an individual, which is odorless, propellant-free, and has a pH of about 4.5 to about 7.5, and which comprises: (A) at least about 85 wt. % of water; (B) about 0.001 to about 2 wt. % of solid particles of triamcinolone acetonide medicament; (C) about 1 to about 5 wt. % of a suspending agent comprising a mixture of about 85 to 95 wt. % of microcrystalline cellulose and about 5 to about 15 wt. % of carboxymethyl cellulose based on the weight of the mixture, the amount of suspending agent being effective to maintain said solid particles dispersed uniformly in the composition and to impart to the composition the following thixotropic properties: (i) the viscosity of the composition in unsheared form is about 400 to about 800 cp; (ii) as the composition is subjected to shear (shaken) in preparation for spraying, the viscosity of the composition is about 50 to about 200 cp and such that the composition in the form of a mist flows readily into the nasal passages for deposit on the mucosal surfaces of the nasal cavity; and (iii) in deposited form on the mucosal surfaces, the viscosity of the composition is about 400 to about 800 cp and such that it resists being cleared from the mucosal surfaces by the inherent mucocillary forces which are present in the nasal cavity; and (D) about 0.004 to about 0.02 wt. % of a quaternary ammonium compound that has anti-microbial properties; and (E) about 0.01 to about 0.5 wt. % of a chelating agent.

6. A composition according to claim 5 wherein said quaternary ammonium compound is benzalkonium chloride and said chelating agent is disodium ethylenediamine tetraacetate.

7. A composition according to claim 5 having about 0.001 to about 0.01 wt. % of dispersing agent which is effective in wetting the particles of medicament.

8. A composition according to claim 7 wherein said dispersing agent is Polysorbate 80™.

9. A composition according to claim 5 including dextrose.

10. The composition of claim 5 wherein said solid particles of medicament have an average size of about 1 to about 20 microns.

11. A product comprising an aqueous pharmaceutical composition comprising a medicament in the form of solid particles of triamcinolone acetonide, a dispersing agent for wetting said particles, and a suspending agent for maintaining said particles substantially uniformly dispersed in the composition and for imparting to the composition thixotropic properties, prepared by a process comprising: (A) providing a suspension of said particles and said dispersing agent; (B) providing a thixotropic aqueous suspension comprising said suspending agent; and (C) combining each of the suspensions by introducing one of the suspensions into the bottom of the other suspension.

12. The product of claim 11 wherein the suspensions are combined by introducing the suspension of (A) into the bottom of the suspension of (B).

13. The product of claim 12 wherein the suspensions are combined by introducing the suspension of (A) into the bottom of the suspension of (B) by pumping said suspension of (A) into the bottom of said suspension of (B).

14. The product of claim 11 wherein an aqueous solution of a quaternary compound is added to the suspension of (A) and an iso-osmotic agent and a chelating agent are added to the suspension of (B) prior to combining the suspension of (A) and (B).

15. A method for preparing an aqueous pharmaceutical composition comprising a medicament in the form of solid particles of triamcinolone acetonide, a dispersing agent for wetting said particles, and a suspending agent for maintaining said particles substantially uniformly dispersed in the composition and for imparting to the composition thixotropic properties, said method comprising: (A) providing an aqueous suspension of said particles and said dispersing agent; (B) providing a thixotropic aqueous suspension comprising said suspending agent; and (C) combining each of the suspensions by introducing one of the suspensions into the bottom of the other suspension.

16. The method of claim 15 wherein said dispersing agent is 80™.

17. The method of claim 15 wherein said suspending agent is a mixture of microcrystalline cellulose and carboxymethylcellulose sodium.

18. A method according to claim 15 wherein the suspension of particles is introduced into the bottom of the thixotropic suspension.

19. A method according to claim 15 wherein said dispersing agent is Polysorbate 80™ and wherein said suspension of (A) further comprises a quaternary ammonium antimicrobial agent and wherein the suspension of (B) further comprises a chelating agent and an anti-osmotic agent.

20. A method according to claim 19 wherein the antimicrobial agent consists essentially of benzalkonium chloride, the chelating agent consists essentially of EDTA and the anti-osmotic agent consists essentially of dextrose.

21. A method for treating allergic rhinitis in an individual comprising applying to the mucosal surfaces of the nasal cavities of an individual a composition according to claim 5 by spraying a dose of the composition into each of the nasal cavities of the individual, said dose containing a pharmaceutically effective amount of said medicament and depositing pharmaceutically effective amounts of the medicament on each of the mucosal surfaces of the anterior regions of the nose, the frontal sinus and the maxillary sinuses and on each of the mucosal surfaces which overlie the turbinates covering the conchas and such that pharmaceutically effective amounts of the medicament are retained on each of said mucosal surfaces for at least about an hour.

22. A method according to claim 21 wherein said quaternary ammonium compound is benzalkonium chloride, and said chelating agent is disodium ethylenediamine tetraacetate.

23. A method according to claim 21 wherein the composition which is applied to said surfaces includes about 0.001 to about 0.01 wt. % of dispersing agent which is effective in wetting the particles of medicament.

24. A method according to claim 23 wherein said dispersing agent is Polysorbate 80™.

25. A method according to claim 21 wherein the dose of composition applied to each of the nasal cavities comprises about 200 to about 450 mcg of medicament.

26. A method according to claim 21 wherein said composition is applied once daily to each of the nasal cavities of the individual in an amount which includes about 100 to about 130 mcg of said medicament.

27. A method according to claim 26 wherein said composition is applied by use of a precompression pump.

28. The method according to claim 26 wherein said composition comprises triamcinolone acetonide, a mixture of microcrystalline cellulose and carboxymethyl cellulose sodium, Polysorbate 80™, disodium ethylenediamine tetraacetate, benzalkonium chloride, dextrose and purified water.

29. A method of treatment according to claim 21 wherein said allergic rhinitis is seasonal allergic rhinitis.

30. A method of treatment according to claim 21 wherein said allergic rhinitis is perennial allergic rhinitis.

31. A method of treatment according to claim 21 wherein at least about 47% of the total medicament remains deposited in the frontal cavity of the individual two hours after administration.

32. A method of treatment according to claim 21 wherein at least about 23% of the total medicament remains deposited in the inferior concha region of the individual two hours after administration.

33. A method of treatment according to claim 21 wherein at least about 6% of the total medicament remains deposited in the superior concha region of the individual two hours after administration.

34. A method for applying solid particles of triamcinolone acetonide to the mucosal surfaces of the nasal cavities comprising spraying a dose of an aqueous pharmaceutical composition containing said medicament into each of the nasal cavities, said dose containing a pharmaceutically effective amount of triamcinolone acetonide, said composition including also a suspending agent in an amount which is effective in maintaining said particles dispersed uniformly in the composition and in imparting to the composition thixotropic properties such that pharmaceutically effective amounts of triamcinolone acetonide are deposited on each of the mucosal surfaces of the anterior regions of the nose, the frontal sinus and the maxillary sinuses, and on each of the mucosal surfaces which overlie the turbinates covering the conchas and such that portions of said amounts are retained on each of said mucosal surfaces for at least about an hour.

35. A method according to claim 34 wherein the viscosity of the composition in unsheared form is about 400 to about 1000 centipoises and wherein the viscosity of the composition when shaken is about 50 to about 200 centipoises.

* * * * *